(12) United States Patent
Lauria

(10) Patent No.: US 9,044,224 B2
(45) Date of Patent: Jun. 2, 2015

(54) BARBED MEDICAL DEVICE AND METHOD

(75) Inventor: Paul Lauria, Clinton, CT (US)

(73) Assignee: Covidien LP, Mansfield, MA (US)

(*) Notice: Subject to any disclaimer, the term of this patent is extended or adjusted under 35 U.S.C. 154(b) by 260 days.

(21) Appl. No.: 13/047,880

(22) Filed: Mar. 15, 2011

(65) Prior Publication Data

US 2011/0251640 A1  Oct. 13, 2011

Related U.S. Application Data

(60) Provisional application No. 61/323,158, filed on Apr. 12, 2010.

(51) Int. Cl.
*A61B 17/04* (2006.01)
*A61B 17/06* (2006.01)
*A61B 17/00* (2006.01)

(52) U.S. Cl.
CPC ..... *A61B 17/06166* (2013.01); *Y10T 428/2976* (2015.01); *Y10T 428/2936* (2015.01); *A61B 2017/06176* (2013.01); *A61B 2017/00526* (2013.01)

(58) Field of Classification Search
CPC .............. A61B 17/06166; A61B 2017/00526; A61B 2017/06176; Y10T 428/2936; Y10T 428/2976
USPC ................. 606/151, 215, 221, 228–232, 224; 256/6–9; 428/100, 222
See application file for complete search history.

(56) References Cited

U.S. PATENT DOCUMENTS

| 3,657,056 | A |   | 4/1972  | Winston et al.        |         |
|-----------|---|---|---------|-----------------------|---------|
| 3,986,331 | A | * | 10/1976 | Brumlik               | 428/222 |
| 4,024,871 | A |   | 5/1977  | Stephenson            |         |
| 4,198,734 | A | * | 4/1980  | Brumlik               | 428/100 |
| 4,259,959 | A | * | 4/1981  | Walker                | 606/221 |
| 4,548,202 | A | * | 10/1985 | Duncan                | 606/221 |
| 5,019,093 | A |   | 5/1991  | Kaplan et al.         |         |
| 5,059,213 | A |   | 10/1991 | Chesterfield et al.   |         |
| 5,123,913 | A |   | 6/1992  | Wilk et al.           |         |
| 5,133,738 | A | * | 7/1992  | Korthoff et al.       | 606/224 |
| 5,181,923 | A |   | 1/1993  | Chesterfield et al.   |         |
| 5,226,912 | A |   | 7/1993  | Kaplan et al.         |         |
| 5,236,563 | A |   | 8/1993  | Loh                   |         |
| 5,261,886 | A |   | 11/1993 | Chesterfield et al.   |         |
| 5,306,289 | A |   | 4/1994  | Kaplan et al.         |         |
| 5,318,575 | A |   | 6/1994  | Chesterfield et al.   |         |

(Continued)

FOREIGN PATENT DOCUMENTS

DE  10 2007 058256 A1   5/2009
EP       0 499 048 A1   8/1992

(Continued)

OTHER PUBLICATIONS

European Search Report for EP 11250457.6-1269 date of completion is Jul. 19, 2011 (3 pages).

(Continued)

*Primary Examiner* — Julian W Woo

(57) ABSTRACT

Barbed medical devices include a multifilament elongate body and a monofilament fragment. The multifilament elongate body has an outer surface. The monofilament fragment has a first portion positioned within the multifilament elongate body and at least a second portion which extends beyond the outer surface of the multifilament elongate body to form a barb.

11 Claims, 10 Drawing Sheets

(56) References Cited

U.S. PATENT DOCUMENTS

| | | |
|---|---|---|
| 5,342,376 A | 8/1994 | Ruff |
| 5,370,031 A | 12/1994 | Koyfman et al. |
| 5,383,387 A | 1/1995 | Chesterfield et al. |
| 5,417,700 A | 5/1995 | Egan |
| 5,569,302 A | 10/1996 | Proto et al. |
| 5,662,682 A | 9/1997 | Chesterfield et al. |
| 5,667,528 A | 9/1997 | Colligan |
| 5,695,879 A | 12/1997 | Goldmann et al. |
| 5,814,056 A | 9/1998 | Prosst et al. |
| 5,893,880 A | 4/1999 | Egan et al. |
| 5,931,855 A | 8/1999 | Buncke |
| 5,964,765 A | 10/1999 | Fenton, Jr. et al. |
| 6,063,105 A | 5/2000 | Totakura |
| 6,106,505 A | 8/2000 | Modak et al. |
| 6,143,352 A | 11/2000 | Clark et al. |
| 6,165,202 A | 12/2000 | Kokish et al. |
| 6,174,324 B1 | 1/2001 | Egan et al. |
| 6,203,564 B1 | 3/2001 | Hutton et al. |
| 6,217,591 B1 | 4/2001 | Egan et al. |
| 6,235,869 B1 | 5/2001 | Roby et al. |
| 6,241,747 B1 | 6/2001 | Ruff |
| 6,270,517 B1 | 8/2001 | Brotz |
| 6,286,746 B1 | 9/2001 | Egan et al. |
| 6,488,690 B1 | 12/2002 | Morris et al. |
| 6,506,197 B1 | 1/2003 | Rollero et al. |
| 6,592,515 B2 * | 7/2003 | Thierfelder et al. ......... 606/151 |
| 6,599,310 B2 | 7/2003 | Leung et al. |
| 6,620,846 B1 | 9/2003 | Jonn et al. |
| 6,692,499 B2 | 2/2004 | Törmälä et al. |
| 6,773,450 B2 | 8/2004 | Leung et al. |
| 6,848,152 B2 | 2/2005 | Genova et al. |
| 6,893,452 B2 * | 5/2005 | Jacobs .......................... 606/215 |
| 6,923,824 B2 | 8/2005 | Morgan et al. |
| 7,056,331 B2 | 6/2006 | Kaplan et al. |
| 7,090,111 B2 | 8/2006 | Egan et al. |
| 7,225,512 B2 | 6/2007 | Genova et al. |
| 7,226,468 B2 | 6/2007 | Ruff |
| 8,083,770 B2 * | 12/2011 | Ruff et al. .................... 606/232 |
| 8,118,834 B1 * | 2/2012 | Goraltchouk et al. ........ 606/228 |
| 2002/0077661 A1 | 6/2002 | Saadat |
| 2002/0177876 A1 | 11/2002 | Roby et al. |
| 2003/0074023 A1 | 4/2003 | Kaplan et al. |
| 2003/0097148 A1 | 5/2003 | Valimaa et al. |
| 2003/0149447 A1 | 8/2003 | Morency et al. |
| 2004/0010275 A1 | 1/2004 | Jacobs et al. |
| 2004/0039415 A1 | 2/2004 | Zamierowski |
| 2004/0060409 A1 | 4/2004 | Leung et al. |
| 2004/0060410 A1 | 4/2004 | Leung et al. |
| 2004/0087974 A1 | 5/2004 | Bittar |
| 2004/0088003 A1 | 5/2004 | Leung et al. |
| 2004/0122451 A1 | 6/2004 | Wood |
| 2004/0153125 A1 | 8/2004 | Roby |
| 2004/0162580 A1 | 8/2004 | Hain |
| 2004/0226427 A1 | 11/2004 | Trull et al. |
| 2005/0033367 A1 | 2/2005 | Leung et al. |
| 2005/0165448 A1 | 7/2005 | Egan et al. |
| 2005/0209639 A1 | 9/2005 | Gidwani et al. |
| 2005/0216058 A1 | 9/2005 | Egan et al. |
| 2005/0267479 A1 | 12/2005 | Morgan et al. |
| 2005/0267531 A1 | 12/2005 | Ruff et al. |
| 2006/0111734 A1 | 5/2006 | Kaplan et al. |
| 2006/0111742 A1 | 5/2006 | Kaplan et al. |
| 2006/0116718 A1 | 6/2006 | Leiboff |
| 2006/0135994 A1 | 6/2006 | Ruff et al. |
| 2006/0135995 A1 | 6/2006 | Ruff et al. |
| 2007/0005109 A1 | 1/2007 | Popadiuk et al. |
| 2007/0005110 A1 | 1/2007 | Collier et al. |
| 2007/0021780 A1 | 1/2007 | Harrington et al. |
| 2007/0065663 A1 | 3/2007 | Trull et al. |
| 2007/0187861 A1 | 8/2007 | Genova et al. |
| 2007/0224237 A1 | 9/2007 | Hwang et al. |
| 2007/0257395 A1 | 11/2007 | Lindh |
| 2008/0058869 A1 | 3/2008 | Stopek et al. |
| 2008/0082113 A1 | 4/2008 | Bishop |
| 2008/0109036 A1 | 5/2008 | Stopek et al. |
| 2008/0195147 A1 | 8/2008 | Stopek |
| 2008/0221618 A1 | 9/2008 | Chen |
| 2008/0255611 A1 | 10/2008 | Hunter |
| 2008/0281357 A1 | 11/2008 | Sung |
| 2008/0312688 A1 | 12/2008 | Nawrocki |
| 2009/0076543 A1 | 3/2009 | Maiorino et al. |
| 2009/0105753 A1 | 4/2009 | Greenhalgh et al. |
| 2009/0140012 A1 | 6/2009 | Greer, Jr. |
| 2009/0210003 A1 | 8/2009 | Sulamanidze et al. |
| 2009/0210006 A1 | 8/2009 | Cohen et al. |
| 2009/0248066 A1 | 10/2009 | Wilkie |
| 2009/0287245 A1 | 11/2009 | Ostrovsky |
| 2010/0084780 A1 | 4/2010 | Lindh, Sr. |
| 2010/0275750 A1 | 11/2010 | Maiorino et al. |
| 2011/0046669 A1 | 2/2011 | Goraltchouk |
| 2011/0125188 A1 | 5/2011 | Goraltchouk |
| 2011/0288583 A1 | 11/2011 | Goraltchouk |
| 2012/0046675 A1 | 2/2012 | Bishop |

FOREIGN PATENT DOCUMENTS

| | | |
|---|---|---|
| EP | 0 632 999 A1 | 1/1995 |
| EP | 0 647 452 A1 | 4/1995 |
| EP | 1 656 890 A2 | 5/2006 |
| EP | 1 669 093 A1 | 6/2006 |
| EP | 2 036 502 A2 | 3/2009 |
| WO | WO 98/00065 | 1/1998 |
| WO | WO 98/52473 | 11/1998 |
| WO | WO 99/52451 | 10/1999 |
| WO | WO 00/57933 | 10/2000 |
| WO | WO 01/52751 A1 | 7/2001 |
| WO | WO 03/001979 A2 | 1/2003 |
| WO | WO 03/017850 A2 | 3/2003 |
| WO | WO 2004/014236 A1 | 2/2004 |
| WO | WO 2004/030520 A2 | 4/2004 |
| WO | WO 2004/030704 A2 | 4/2004 |
| WO | WO 2004/030705 A2 | 4/2004 |
| WO | WO 2004/045663 A1 | 6/2004 |
| WO | WO 2004/066927 A2 | 8/2004 |
| WO | WO 2005/079388 A2 | 9/2005 |
| WO | WO 2006/079469 A1 | 8/2006 |
| WO | WO2007/131019 A2 | 11/2007 |
| WO | WO 2007/133103 A1 | 11/2007 |
| WO | WO 2008/042909 A2 | 4/2008 |
| WO | WO2008/042992 A2 | 4/2008 |
| WO | WO 2008/107919 A1 | 9/2008 |
| WO | WO2008/112417 A2 | 9/2008 |
| WO | WO 2008/117328 A2 | 10/2008 |
| WO | WO2008/141034 A1 | 11/2008 |
| WO | WO 2008/141034 A1 | 11/2008 |
| WO | WO2008/157142 A2 | 12/2008 |
| WO | WO 2009/105663 A2 | 8/2009 |
| WO | WO 2009/129251 A2 | 10/2009 |
| WO | WO2009/132284 A2 | 10/2009 |
| WO | WO2009/140012 A1 | 11/2009 |

OTHER PUBLICATIONS

European Search Report EP 12 16 5912 dated Jul. 18, 2012.
European Search Report EP 12 16 9370 dated Sep. 12, 2012.

* cited by examiner

BARBED MEDICAL DEVICE AND METHOD

CROSS-REFERENCE TO RELATED APPLICATIONS

This application claims the benefit of and priority to U.S. Provisional Patent Application No. 61/323,158, filed Apr. 12, 2010, the entire disclosure of which is incorporated by reference herein.

TECHNICAL FIELD

The present disclosure relates generally to barbed medical devices. In particular, the present disclosure relates to barbed sutures and methods of forming barbs on sutures.

BACKGROUND OF RELATED ART

Sutures are known for use in medical procedures. While a monofilament suture may be suitable for certain wounds, for others, a multifilament suture may be desired. Multifilament sutures may exhibit better handling characteristics and be more supple than monofilament sutures.

Barbed sutures are also known. Both the type of suture and the configuration of barbs on the suture may be designed to optimize tissue holding for a particular indication. In some situations a random configuration of barbs on the exterior surface of the suture may be preferred to achieve optimal wound closure. In other circumstances, where the wound or tissue repair needed is relatively small, a reduced number of barbs may be desired. In still other circumstances, a bi-directional barbed suture may be desirable to permit passing of the suture through tissue in one direction over a portion of the suture and permit passing of the suture through tissue in a second direction over another portion of the suture.

While various methods of forming barbs on sutures have been proposed, such methods may be difficult or costly to implement. Thus, there remains room for improvement with respect to barbed sutures and methods for making them.

SUMMARY

Barbed medical devices in accordance with the present disclosure include a monofilament fragment and a multifilament elongate body. The monofilament fragment includes a first portion positioned within the multifilament elongate body and a second portion extending beyond the outer surface of the multifilament elongate body.

Methods of forming the present barbed medical devices include positioning a monofilament fragment at least partially within an elongate body formed from a plurality of filaments such that a first portion of the monofilament fragment is positioned within the multifilament elongate body and a second portion of the monofilament fragment extends beyond the outer surface of the multifilament elongate body. The monofilament fragment is thus secured within the elongate body such that a portion of the monofilament fragment extends from the outer surface of the multifilament elongate body to function as a barb on the medical device.

BRIEF DESCRIPTION OF DRAWINGS

Various embodiments of the present disclosure will be described herein below with reference to the figures wherein.

DETAILED DESCRIPTION

The present medical devices include a multifilament elongate body having at least one monofilament fragment extending from an outer surface of the multifilament elongate body. A first portion of the monofilament fragment is positioned within the multifilament elongate body and a second portion of the monofilament fragment is positioned beyond the outer surface of the multifilament elongate body. The portion of the monofilament fragment positioned within the multifilament elongate body secures the monofilament fragment to the multifilament elongate body. The second portion of the monofilament fragment extends beyond the outer surface of the multifilament elongate body forming a barb on the medical device. The monofilament fragment may have more than one portion that extends beyond the outer surface of the elongate body.

As used herein, the term "monofilament fragment" means a discrete length of fibrous material that is separately formed and distinct from the elongate body prior to forming the medical device.

In general, methods of forming the barbed medical device may include injecting or inserting fragments of monofilament into a multifilament elongate body such that the a portion of the fragments penetrate and are secured within the elongate body and a portion of the monofilament fragment extends beyond the outer surface of the multifilament elongate body forming a barb on the medical device. The monofilament may be positioned within the multifilament elongate body at a desired orientation relative to the outer surface of the multifilament elongate body to function as a barb. Alternatively, the orientation of the portion of the monofilament fragment that extends beyond the outer surface of the multifilament elongate body may be changed after positioning of the monofilament fragment to provide a desired barb configuration.

Figure 1A:
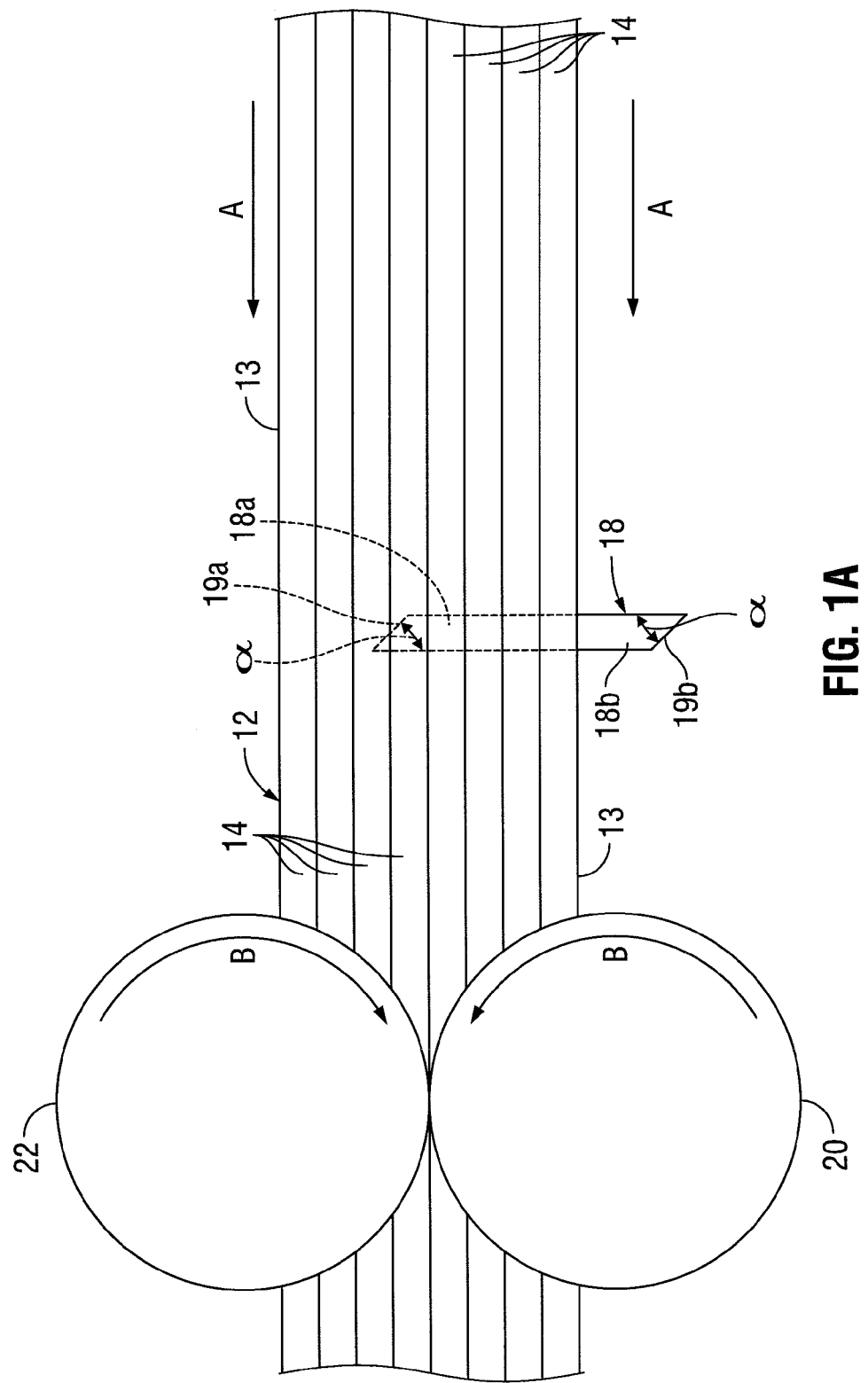
FIG. 1A illustrates a medical device prior to calendering in accordance with the present disclosure.
Figure 1B:
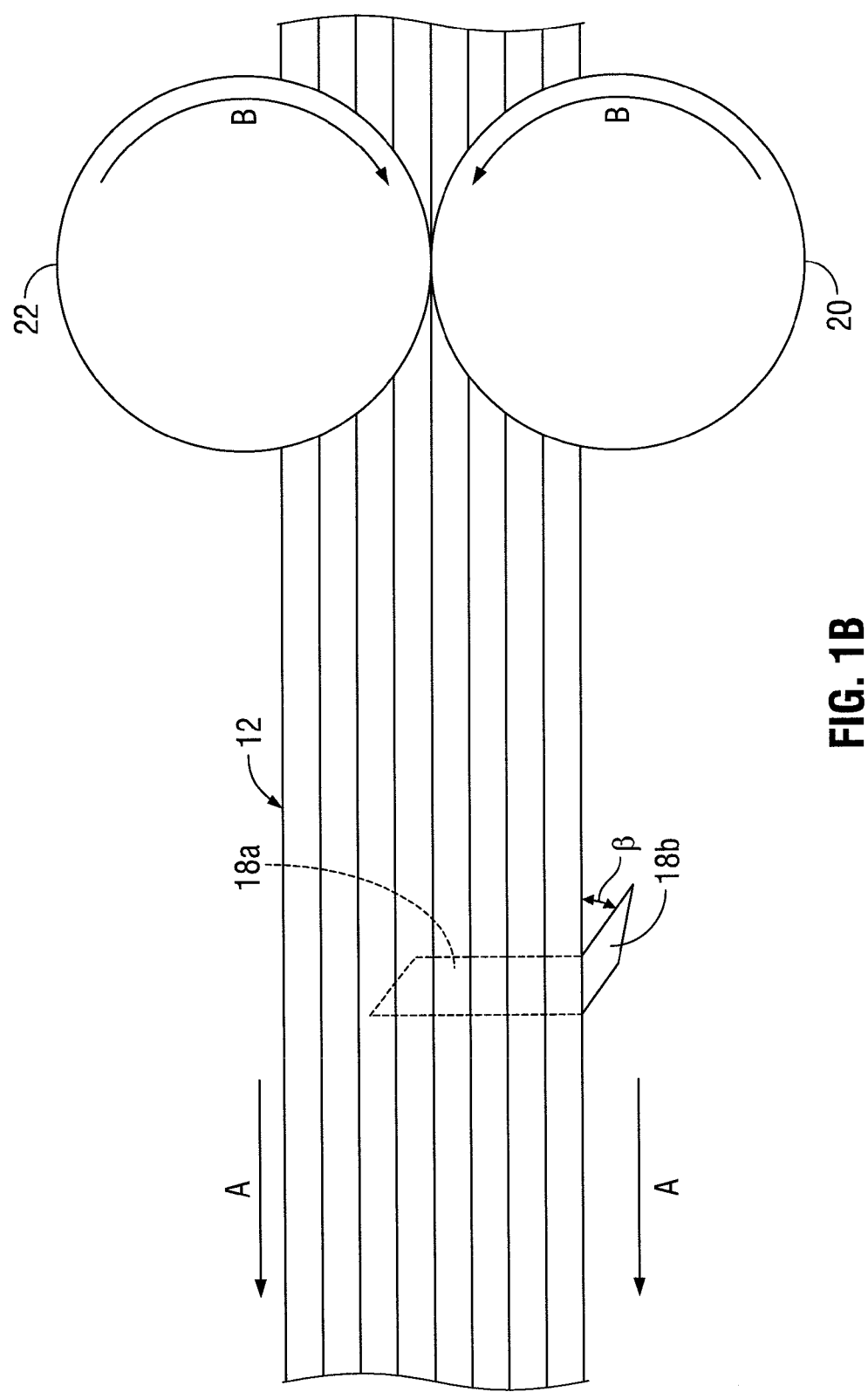
FIG. 1B illustrates an embodiment of the medical device of FIG. 1A following calendering in accordance with the present disclosure.

Referring in detail to the drawings in which like reference numerals are applied to like elements in the various views, FIGS. 1A and 1B illustrate the making of a barbed medical device in accordance with one embodiment of the present disclosure. As seen in FIG. 1A, multifilament elongate body 12 may include a plurality of aligned filaments 14. Monofilament fragment 18 is positioned at least partially within multifilament elongate body 12. Fragment 18 may be a monofilament including a first portion 18a positioned within the multifilament elongate body 12. A second portion 18b of monofilament fragment 18 extends beyond the outer surface 13 of multifilament elongate body 12.

One or both of ends 19a, 19b of fragment 18 may be angled. The angle "α" at ends 19a, 19b of fragment 18 may be the same or different at each end. In embodiments, angle "α" may be from about 5° to about 90°, in embodiments from about 25° to about 65°. End 19a of fragment 18 may advantageously be angled to assist with penetrating multifilament elongate body 12 during manufacture of the present barbed medical device and, in embodiments, cutting through one or more individual filaments 14 of multifilament elongate body 12 that may be encountered during insertion of a portion of the monofilament fragment 18 into the multifilament elongate body 12.

End 18b of monofilament fragment 18 may be deformed by the application of heat and/or pressure to form a desired angle relative to outer surface 13 of multifilament elongate body 12. For example, multifilament elongate body 12 may be moved in the direction indicated by arrows "A" in FIG. 1A and passed through a pair of rollers 20, 22 which may be rotating in the direction indicated by arrows "B". Rollers 20, 22 may apply pressure and/or heat to deform second portion 18b of monofilament fragment 18 as shown in FIG. 1B. The surfaces of rollers 20, 22 advantageously may be contoured to match the contour of outer surface 13 of multifilament elongate body 12 to facilitate uniform application of heat and/or pressure to the multifilament elongate body 12.

As seen in FIG. 1B, the deformed end 18b of monofilament fragment 18 may form an angle "β" with outer surface 13 of multifilament elongate body 12. In embodiments, angle β may be from about 5° to about 60°, in embodiments from about 10° to about 30°. The angle formed may be controlled by varying one or more of: the speed at which elongate multifilament body 12 is passed though calendar rollers 20, 22; the temperature of calendar rollers 20, 22; the pressure applied by calendar rollers 20, 22; the rate at which calendar rollers 20, 22 rotate; and the characteristics (e.g., material(s) of construction, crystallinity, etc.) of monofilament fragment 18. It is further contemplated that the barbs may be formed at a consistent angle or at different angles along the length of the medical device.

Prior to or after positioning of monofilament fragment 18, filaments 14 may be joined to one another using methods known to those skilled in the art, such as, for example, by braiding, thereby securing monofilament fragment 18 to multifilament elongate body 12. Filaments 14 may be joined along their entire length or, alternatively, may be joined at select locations chosen to secure monofilament fragment 18 at its position within filaments 14. In embodiments, the filaments 14 forming the multifilament elongate body 12 may be joined by applying a composition that penetrates between filaments 14. For example, any suitable biocompatible adhesive, such as, an acrylic, an epoxy, a urethane, or other suitable adhesive may be applied to filaments 14 to join them together. In embodiments, the filaments may be joined by heating filaments 14 so that they at least partially fuse together. For example, rollers 20, 22 may apply sufficient heat and pressure to fuse the filaments 14 forming the multifilament elongate body 12. Alternatively, a pair of heated anvils (not shown) may be positioned adjacent the location of monofilament 18 to locally apply sufficient heat and pressure to fuse the filaments 14 forming the multifilament elongate body 12. The temperature required to adhere filaments 14 to one another may vary depending on the type or types of material from which the filaments are formed.

A plurality of monofilament fragments can positioned within the multifilament elongate body in any pattern. The number, configuration and spacing of the monofilament fragments may, for example, create a helical pattern, a linear pattern, a double helix pattern, a random pattern, or any other pattern envisioned by those skilled in the art. Additionally, the distribution of the monofilament fragments may remain relatively constant or may be varied along the length of the multifilament elongate body, thereby allowing the creation of areas with a higher density of barbs and areas with relatively few barbs or even no barbs at all.

Longitudinal spacing between any two barbs generally affects the ability of the barbed device to anchor tissues while maintaining firmness. As barbs are spaced farther apart, tissue-anchoring capacity generally decreases. An increased number of barbs may result in increased tissue holding force. The longitudinal spacing of the barbs may be from about 0.1 mm to about 3 mm, in embodiments, from about 0.5 mm to about 1 mm. Where, as in the prior art, barbs are cut into the surface of a medical device, if barbs are spaced too close, the integrity of the medical device may be jeopardized, which could lead to a tendency of the barbs to peel back and also to a decrease in tensile strength. By eliminating cutting of the elongate body, the present methods of forming barbs on a medical device by positioning monofilament fragments within a multifilament elongate body avoids this potential disadvantage.

In addition, by positioning monofilament fragments of different configuration, barbs of different configurations may easily be provided on a single barbed medical device. For example, a combination of large and small barbs within the same structure may be beneficial, for example when the barbed medical device is used in repair of tissue having differing layer structures. Use of a combination of large and small barbs on the same barbed medical device wherein barb sizes are customized for each tissue layer will ensure maximum anchoring properties.

In embodiments, all of the barbs may be aligned to allow the barbed medical device to move through tissue in one direction and resist moving through tissue in the opposite direction, such as a mono-directional barbed suture. In other embodiments, the barbs may be aligned on a first portion of a length of a barbed medical device to allow movement of a first end of the suture through tissue in one direction, while barbs on a second portion of the length of the barbed medical device may be aligned to allow movement of the second end of the suture in an opposite direction, such as a bidirectional barbed suture.

The filaments of the multifilament elongate body may be made from any biocompatible natural or synthetic material. The material from which the filaments of the multifilament elongate body are formed may be bioabsorbable or non-bioabsorbable. It should of course be understood that any combination of natural, synthetic, bioabsorbable and non-bioabsorbable materials may be used to form the filaments of the multifilament elongate body, either by forming individual filaments from a combination of materials (e.g., heterogeneous filaments such as filaments having a core-shell structure) or by combining individual filaments which each of which are made of a different material (e.g., homogeneous filaments made from a first material with homogenous filaments made from a second material that is different from the first material). In embodiments, the multifilament elongate body includes both bioabsorbable filaments and non-bioabsorbable filaments. In other embodiments, the multifilament elongate body is made entirely from bioabsorbable filaments. In yet other embodiments, the multifilament elongate body is made entirely from non-bioabsorbable filaments.

Absorbable materials are absorbed by biological tissues and disappear in vivo at the end of a given period, which can vary for example from hours to several months, depending on the chemical nature of the material. Absorbable materials include both natural and synthetic biodegradable polymers.

Representative natural biodegradable polymers include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers include polyhydroxy acids prepared from lactone monomers, such as glycolide, lactide, caprolactone, ε-caprolactone, valerolactone, and δ-valerolactone, as well as pluronics, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Suitable non-biodegradable materials which may be utilized to form the filaments of elongate body 12 include polyolefins, such as polyethylene and polypropylene; copolymers of polyethylene and polypropylene, and blends of polyethylene and polypropylene; polyamides (such as nylon); polyamines; polyimines; polyesters such as polyethylene terephthalate; polytetrafluoroethylene; polyether-esters such as polybutester; polytetramethylene ether glycol; 1,4-butanediol; polyurethanes; and combinations thereof. The polypropylene may be isotactic polypropylene or a mixture of isotactic and syndiotactic or atactic polypropylene. Other suitable non-biodegradable materials include silk, collagen, cotton, linen, carbon fibers, and the like. Stainless steel, titanium, NiTi alloys and other metallic materials may also be used to form one or more of filaments of the multifilament elongate body.

Characteristics of the multifilament elongate body, apart from the material of its construction, include: (1) diameter; (2) overall denier; (3) the pattern of the yarns; (4) pick count; (5) the number of yarns comprising the multifilament elongate body; and, (6) the denier of the filaments comprising each yarn.

Diameter—The diameter of the multifilament elongate body may be from about 0.01 to about 1.0 mm or greater. Where the multifilament elongate body in accordance with the present disclosure is a suture, the size of the multifilament elongate body can be expressed in terms of standard sizes, corresponding to certain ranges of diameter (in millimeters), as set forth in the United States Pharmacopoeia (USP). Standard sizes of the multifilament elongate body may thus advantageously be as set forth in Table I:

TABLE I

| USP Suture Size | Diameter (mm) |
|---|---|
| 2 | 0.50-0.599 |
| 1 | 0.40-0.499 |
| 0 (1/0) | 0.35-0.399 |
| 2/0 | 0.30-0.399 |
| 3/0 | 0.20-0.249 |
| 4/0 | 0.15-0.199 |
| 5/0 | 0.10-0.149 |
| 6/0 | 0.070-0.099 |
| 7/0 | 0.50-0.069 |
| 8/0 | 0.40-0.049 |

Overall Denier—In embodiments, the overall denier of the multifilament elongate body can vary from about 25 to about 10,000. Within this range, the ranges of overall denier for various embodiments may be from about 50 to about 125 denier; from above about 200 to about 300 denier; from above about 300 to about 500 denier; from above about 500 to about 800 denier; from above about 800 to about 1500 denier; from above about 1500 to about 2000 denier; or, from above about 2000 to about 3600 denier.

Pattern of the Yarns—Where the multifilament elongate body has a tubular braided structure, the filaments may be yarns that form a criss-cross pattern which may be thought of as confined to the surface of a hollow cylinder which, in the absence of a core component, possesses a lumen which represents a significant percentage of the cross-sectional area of the elongate body. Where the multifilament elongate body has a spiroid braided structure, a pattern of interlocking yarns extend from the surface of cylinder to its center thus providing a solid structure in which the filamentous material of its construction occupies substantially the entire cross-sectional area of the suture with a relatively minor percentage of such area constituting void spaces or interstices between adjacent yarns and fibers.

Pick Count—Pick count is the number of stitches per inch lying in a single line parallel to the longitudinal axis of the multifilament elongate body as viewed from the outer surface of the multifilament elongate body. Suitable pick counts can vary from about 20 to about 100 stitches/inch, in embodiments from about 40 to about 80 stitches/inch and, in other embodiments, from about 50 to about 70 stitches/inch.

The Number of Yarns—The number of yarns employed in the construction of the multifilament elongate body bears some relation to overall body denier, the number of yarns generally increasing with the weight of the multifilament elongate body. Thus, across the range of multifilament elongate body weights (denier) indicated above, the multifilament elongate body may be fabricated with from about 4 up to about 60 yarns, in embodiments from about 6 up to about 30 yarns, with each yarn being constructed from individual filaments having the deniers discussed below.

While the yarns need not be twisted, in embodiments the yarns may be provided with a slight twist so as to minimize snagging during braid construction.

It should, of course, be understood that in embodiments the multifilament elongate body may be formed from a plurality of monofilaments (rather than yarns) that are braided, woven, or the like. In such embodiments, the diameter of the monofilaments may be from about 5 to about 200 denier, in embodiments, from about 10 to about 150 denier.

Individual Filament Denier—The individual filaments comprising each yarn can vary in weight from about 0.2 to about 6.0 denier, in embodiments from about 0.8 to about 3.0 denier and in other embodiments from about 0.8 to about 1.4 denier. The number of such filaments present in a particular yarn will depend on the overall denier of the multifilament elongate body as well as the number of yarns utilized in the construction of the multifilament elongate body.

The filaments that make up the elongate body may be formed using any technique within the purview of those skilled in the art, such as, for example, extrusion, molding and/or solvent casting. The elongate body and/or the filaments may include a yarn made of more than one filament, which may contain multiple filaments of the same or different materials. Where the elongate body is made of multiple filaments, the elongate body may be made using any known technique such as, for example, braiding, weaving or knitting. The filaments may also be combined to produce a non-woven elongate structure. The elongate body may be drawn, oriented, crinkled, twisted, commingled or air entangled to form yarns as part of the elongate body forming process.

The monofilament fragment may be made of any biocompatible material, including any of the materials listed above in connection with the filaments of the multifilament elongate body. The monofilament fragment may be made of the same material as the multifilament elongate body or of a different material. The monofilament fragment can vary in weight from about 25 to about 10,000 denier, in embodiments from about 50 to about 5,000 denier and in other embodiments from about 500 to about 1,000 denier. In embodiments, the ratio of the diameter of the multifilament elongate body to the diameter of the monofilament fragment can be from about 2:1 to about 20:1, in embodiments from about 4:1 to about 10:1.

It should be understood that the monofilament fragment may be a homogenous filament made form a single material or a heterogeneous structure such as a core-shell structure where the core and shell are made from different materials. The monofilament fragment may also be made from a multifilament structure where the multifilaments have been joined together to make a unitary structure, such as, for example by the application of heat or an adhesive (or other binding agent).

Figure 2A:
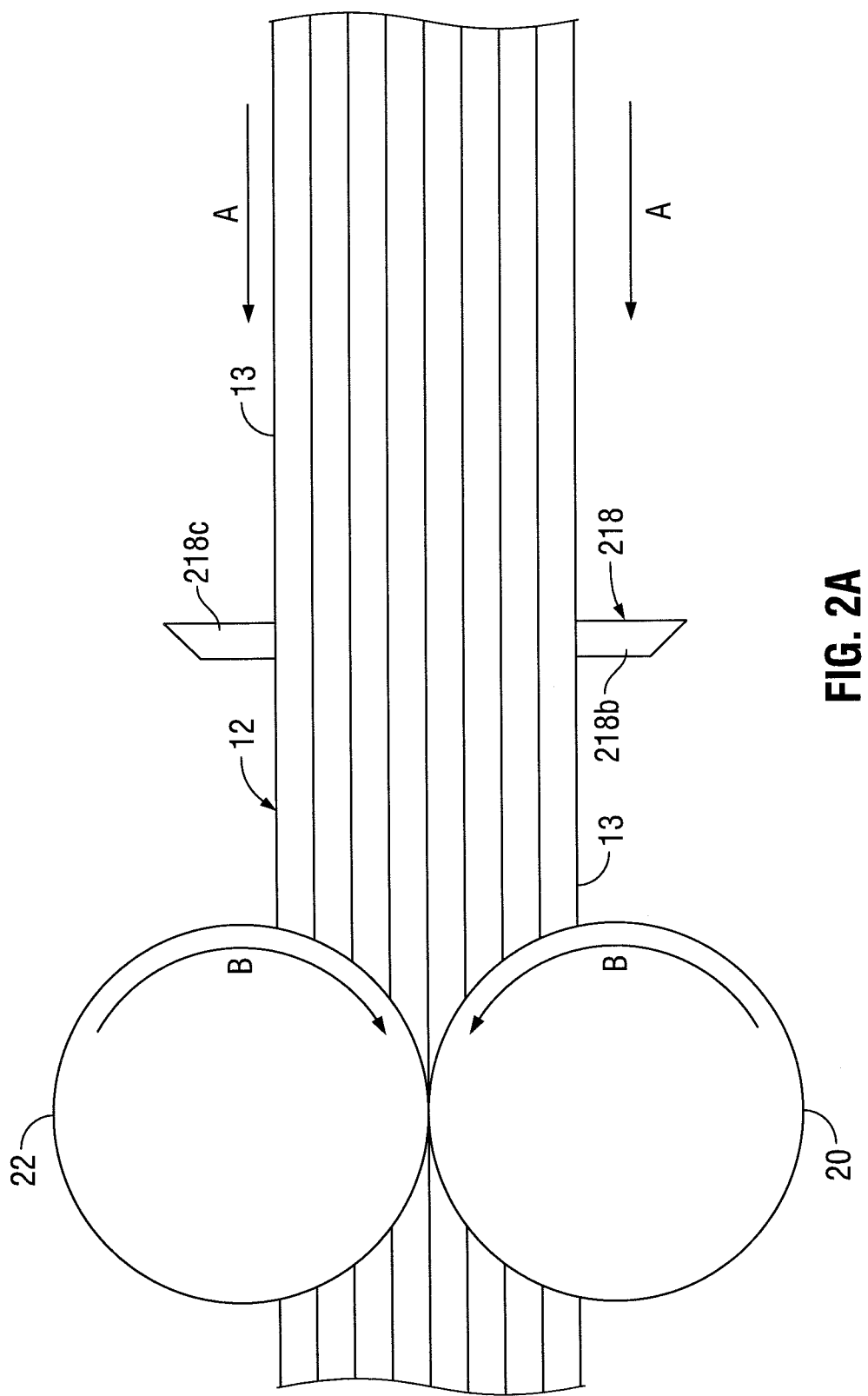
FIG. 2A illustrates another embodiment of medical device prior to calendering in accordance with the present disclosure.
Figure 2B:
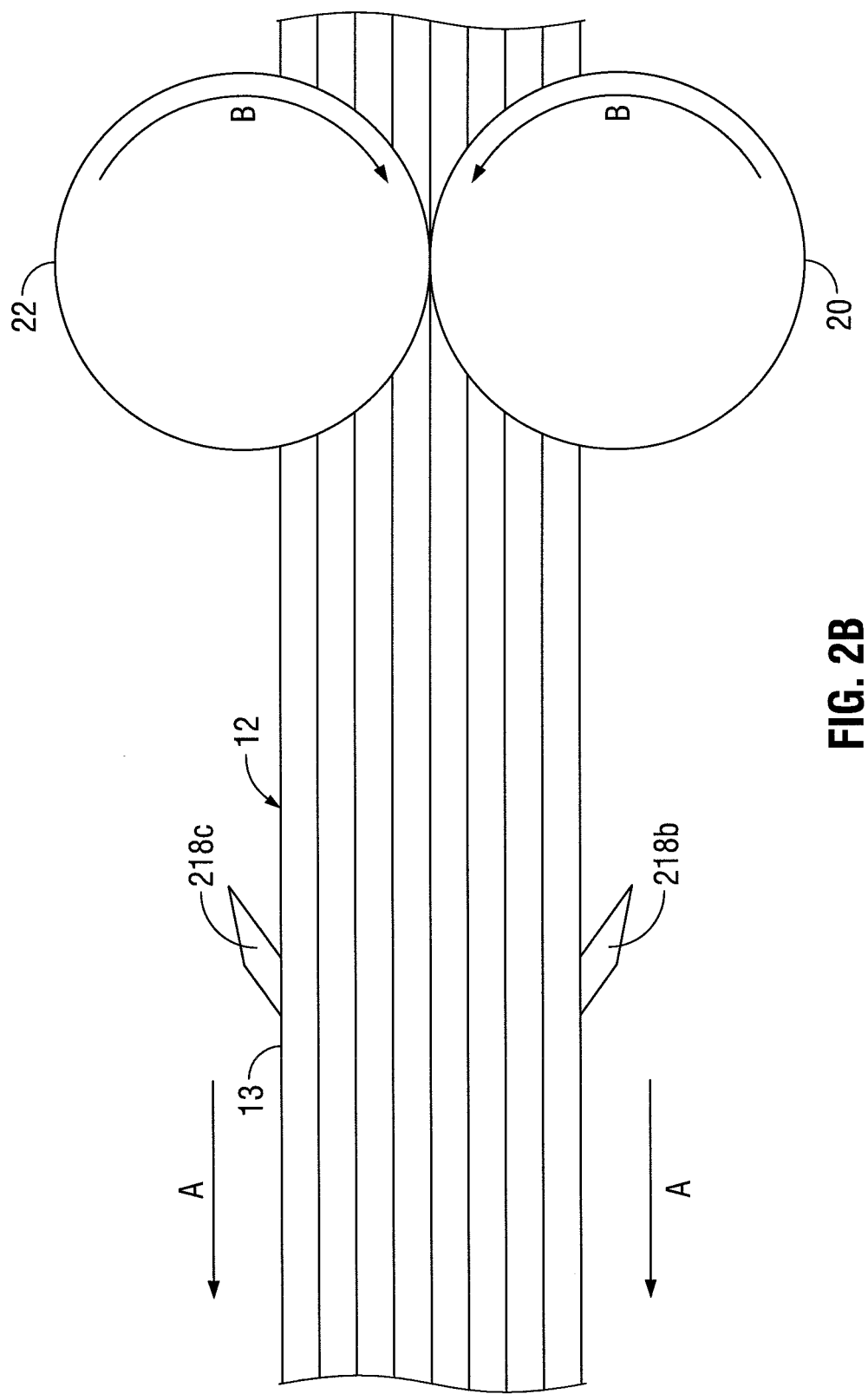
FIG. 2B illustrates an embodiment of the medical device of FIG. 2A following calendering in accordance with the present disclosure.

In embodiments, as shown in FIGS. 2A and 2B, the monofilament fragment 218 may pass entirely through multifilament body 12 and thus include a third portion 218c which extends beyond outer surface 13 of multifilament elongate body 12 at a location remote from the second portion 218b. After passing through rollers 20, 22 in the same manner as described above with respect to FIGS. 1A and 1B, fragment 218 provides two barbs formed by portions 218b and 218c as shown in FIG. 2B.

Figure 3A:
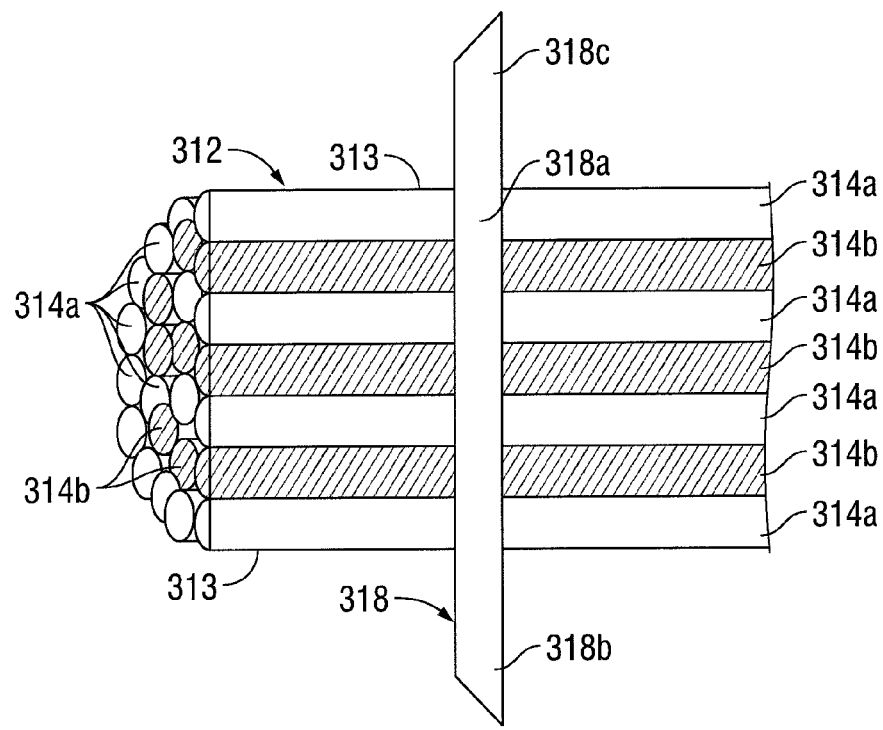
FIG. 3A illustrates a side view cut along an axis of a variation of the embodiment of FIG. 2A with a portion of the elongate body removed.
Figure 3B:
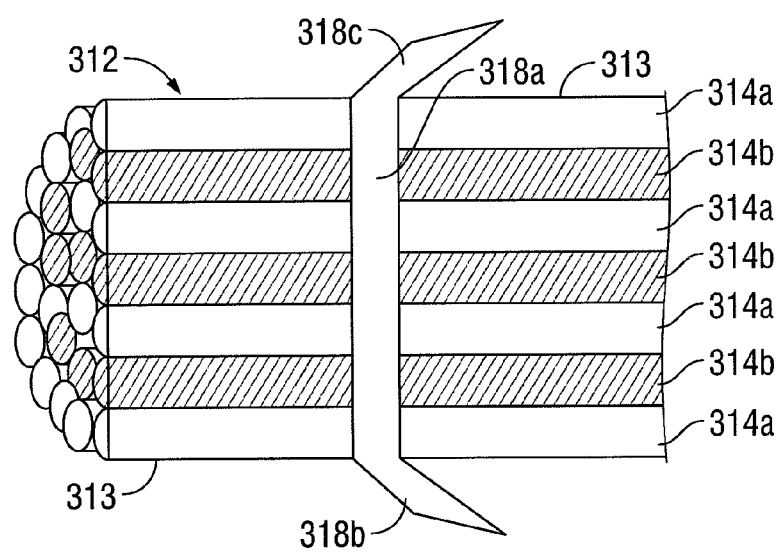
FIG. 3B illustrates a side view cut along an axis of a variation of the embodiment of FIG. 2B with a portion of the elongate body removed.

FIGS. 3A and 3B illustrate a variation of the embodiment of FIGS. 2A and 2B, respectively, showing a cross-sectional view of a portion of elongate body 312. The cross-section is along the longitudinal axis of elongate body 312 to provide a view of fragment 318 passing all of the way through elongate body 312. Portion 318a is positioned within elongate body 312. Portions 318b and 318c are positioned beyond the outer surface 313 of elongate body 312. Elongate body 312 is a heterogeneous structure in FIGS. 3A and 3B, including filaments 314a which are made of a first material and filaments 314b which are made of a second material that is different from the first material.

Figure 4:
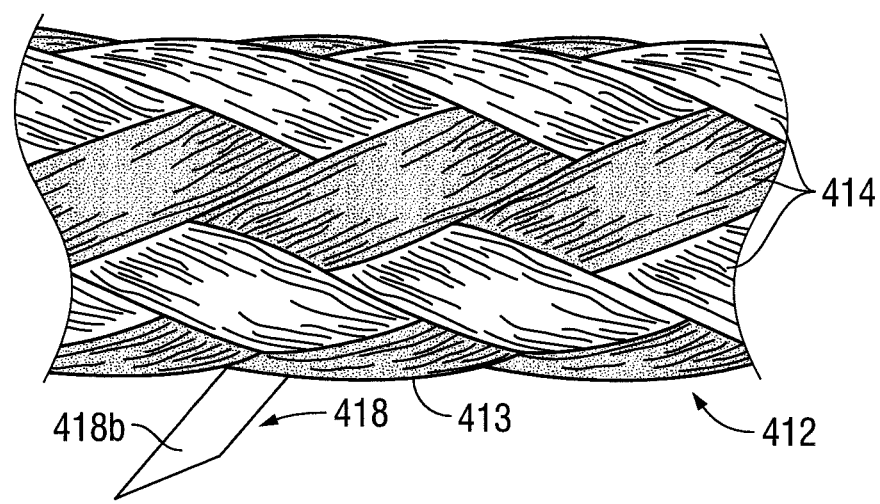
FIG. 4 illustrates a plan view of another embodiment having a braided a multifilament elongate body.

FIG. 4 illustrates an embodiment wherein multifilament elongate body 412 is made up of braided yarns 414. Due to the configuration of the braid, portion 418b of monofilament fragment 418 is positioned at a suitable orientation with respect to outer surface 413 of multifilament elongate body 412 and requires no further reorientation. Monofilament fragment 418 may be secured within multifilament elongate body 412 by the construction of the braid or by any of the methods previously mentioned.

Figure 5A:
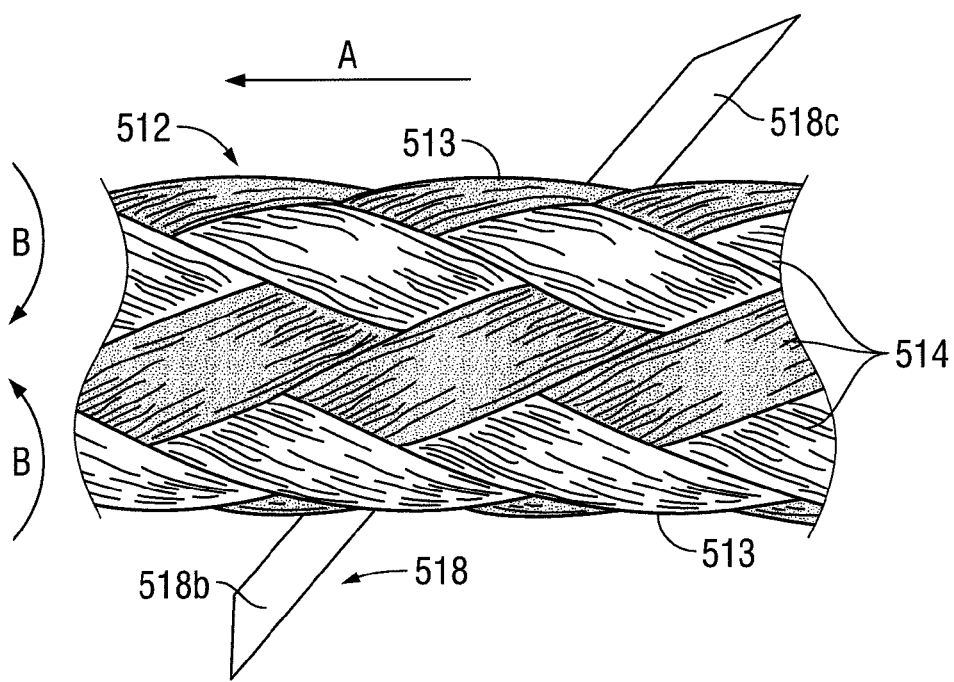
FIG. 5A illustrates a plan view of an embodiment of a monofilament fragment secured within a braided multifilament elongate body before calendering.
Figure 5B:
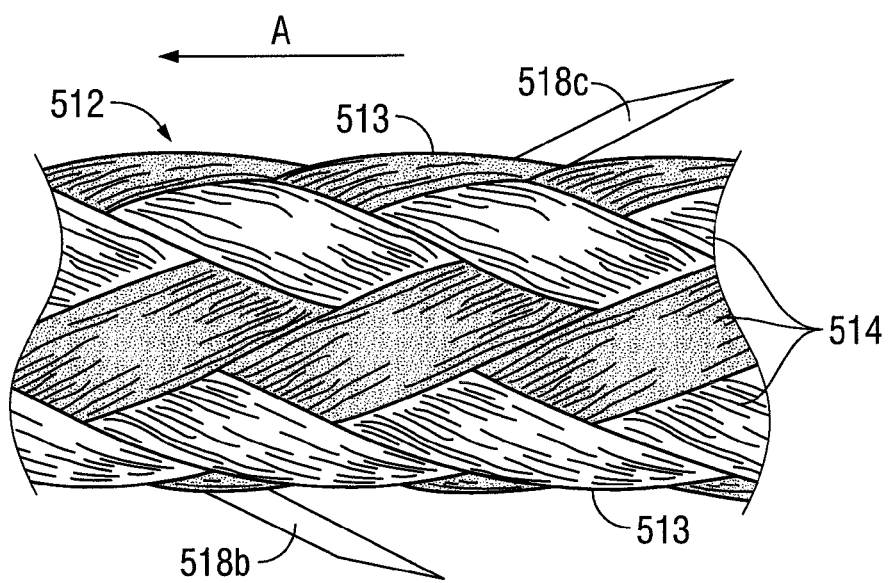
FIG. 5B illustrates a plan view of the embodiment of FIG. 5A after calendering.

FIGS. 5A and 5B illustrate a variation of the embodiment of FIGS. 2A and 2B, respectively wherein monofilament fragment 518 passes entirely through multifilament elongate body 512 which is made up of braided yarns 514. FIG. 5A shows the device prior to passing through rollers (not shown, but rotating in the direction of arrows "B") and FIG. 5B shows the device after moving the device in the direction of arrow "A" and passing the device though rollers thereby changing the orientation of portions 518b and 518c to a desired configuration.

Figure 6:
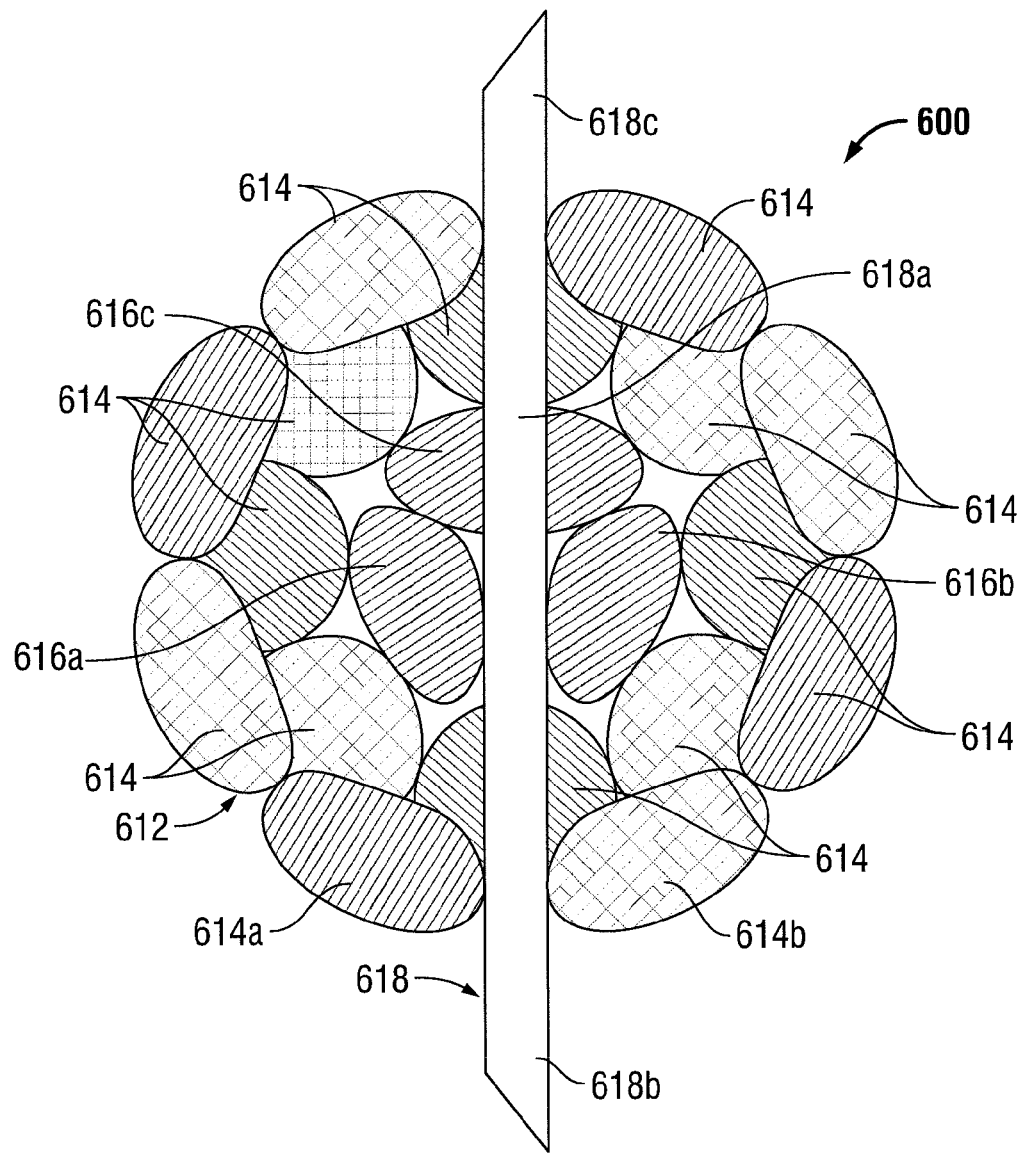
FIG. 6 is a cross-sectional view cut along an axis of yet another embodiment of a medical device in accordance with the present disclosure.

FIG. 6 is a cross-sectional view of a further embodiment of a barbed medical device. The cross-section is transverse to the longitudinal axis of multifilament elongate body 612 to show that in this embodiment multifilament elongate body 612 includes three core filaments 616a, 616b and 616c, and multiple filaments 614 braided to form a sheath around core filaments 616a, 616b and 616c. Monofilament fragment 618 is positioned completely through multifilament elongate body 612, passing between sheath filaments 614a and 614b and through core filament 616c. Portion 618a of fragment 618 is positioned within the multifilament elongate body 612 and portions 618b and 618c of the fragment 618b are positioned beyond the outer surface of the multifilament elongate body 612.

Although the fragment 618 is shown in FIG. 6 as positioned through the center of the core of multifilament elongate body 612, it should of course be understood that the monofilament fragment may be positioned off-center through the multifilament elongate body. For example, monofilament fragment may pass between the sheath and core, rather than through the core.

Figure 7:
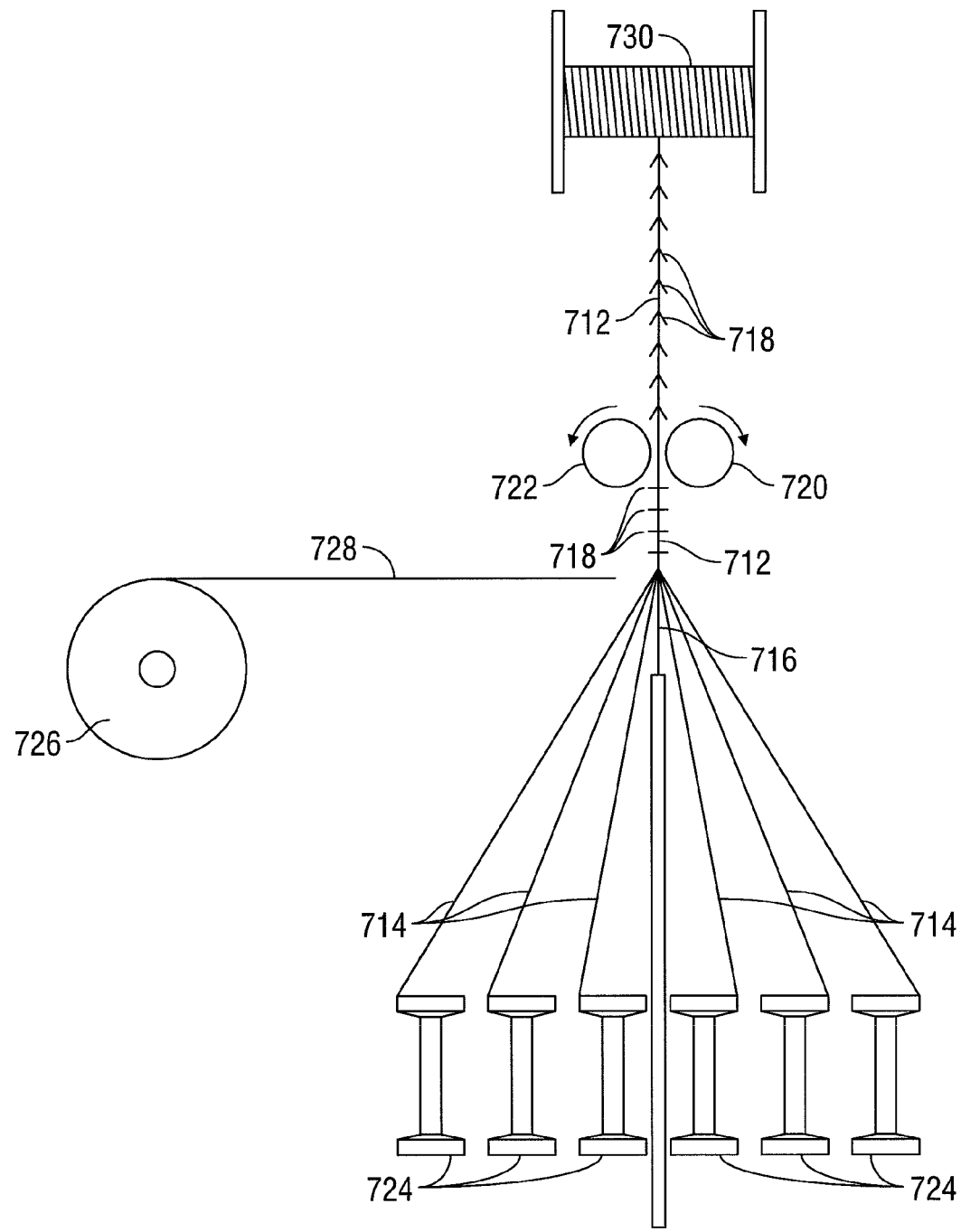
FIG. 7 illustrates an apparatus for carrying out a method of making a medical device in accordance with one embodiment of the present disclosure.

An apparatus suitable for use in making the present barbed medical device where the multifilament elongate body is of a braided construction is shown in FIG. 7. Multiple bobbins 724, including filaments 714 thereon, may be utilized to form a braided sheath about a core 716 to form a multifilament elongate body 712. In embodiments, the fragments 718 may be added to the core 716 and heat set so as not to move while traveling through a tube carrying the core 716. In embodiments, as the multifilament elongate body 712 is formed, a spool 726 of monofilament material 728 is used to generate fragments 718 of monofilament material 728 that are inserted into elongate body 712. It should be understood that the monofilament fragments may be inserted before, during or after braiding of multifilament elongate body 712. In embodiments, a tube or catheter (not shown) which terminates immediately adjacent to filaments 714 may carry monofilament material 728, which is then pushed between filaments 714 or into elongate body 712. The monofilament material 728 is then cut into fragments 718 and advanced again. Next, rollers 720, 722 flatten the fragments 718 in the desired direction forming barbs on multifilament elongate body 712. The barbed medical device may then be wound around a spool 730 or cut to size to be packaged and sterilized using techniques within the purview of one skilled in the art.

It is further contemplated that in embodiments monofilament fragments 718 may be inserted into and heat set within core 716 prior to braiding filaments 714, rather than or in addition to being inserted at the location shown in FIG. 7.

Figure 9:
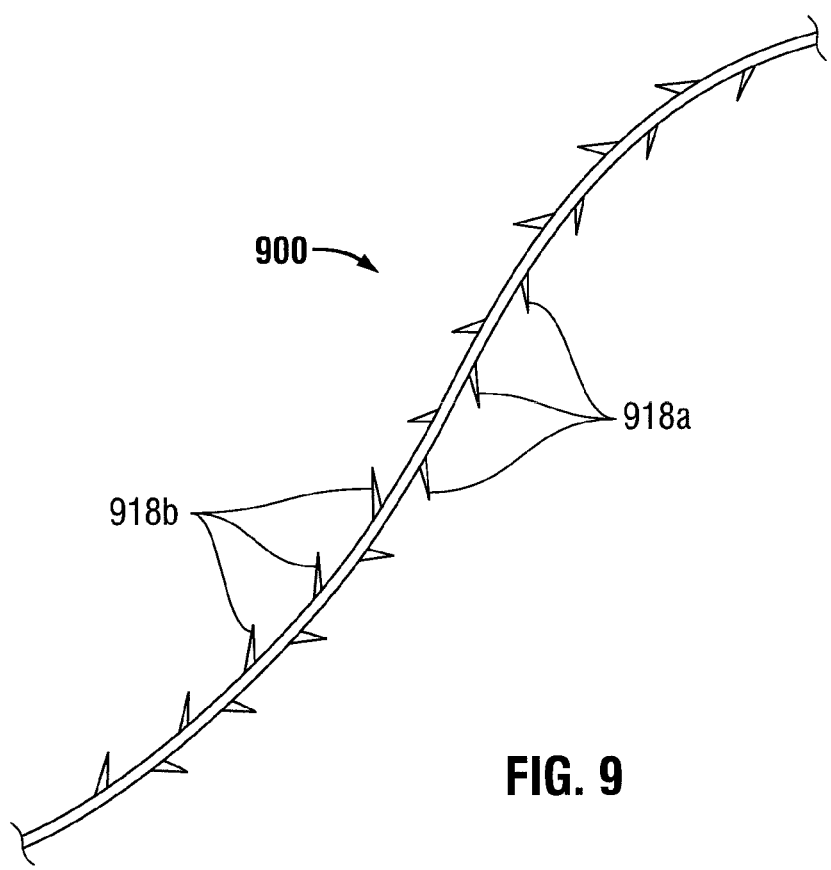
FIG. 9 is a side view of another embodiment of a medical device in accordance with the present disclosure.

As shown in the exemplary embodiment of FIG. 9, a plurality barbs may be formed along the medical device 900 such that some of the barbs 918a are angled toward one end of medical device 900 and other barbs 918b are angled toward the other end of medical device 900 so as to form a bi-directional medical device 900.

The barbed medical device in accordance with the present disclosure may be a braided sutures, multi-filament sutures, surgical fibers, anchors, slit sheets, ribbons, tape, mesh, stent, scaffolds, pledgets, vascular graft, and/or ribbons. The cross-sectional geometry of the medical device may be of any suitable shape, for example, round, square, star shaped, octagonal, rectangular, polygonal and flat.

In embodiments, the present barbed medical devices have their ends being pointed and formed of a material sufficiently stiff to allow for piercing tissue. In other embodiments, where the barbed medical device is a suture, one or both ends of the suture may be armed with a surgical needle. Surgical needles may be attached using any technique within the purview of those skilled in the art. Further, the surgical needle may be coated, the coating allowing for the needle of the surgical needle/barbed suture combination embodiments to be inserted into tissue with less force than if the surgical needle were not coated. The coating may for instance include a silicone-based coating such as, for example the coatings described in U.S. Pat. No. 5,258,013.

Figure 8:
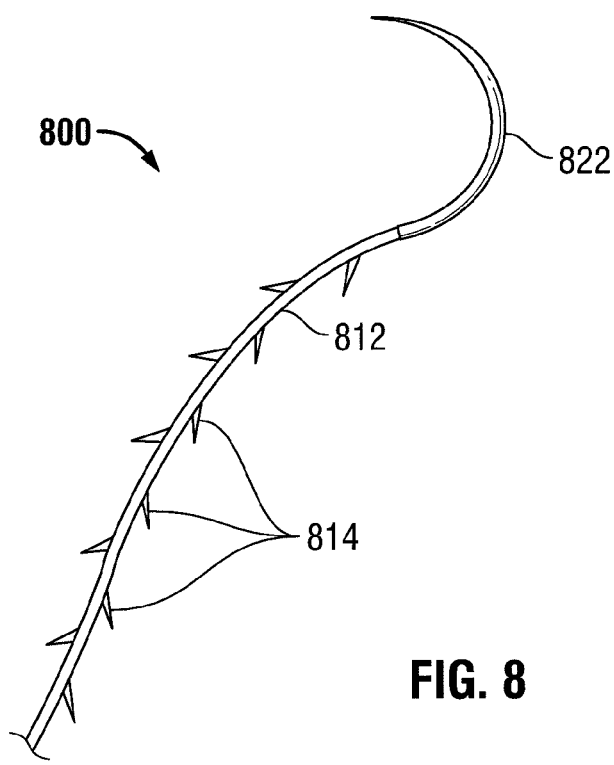
FIG. 8 is a side view of another embodiment of a medical device in accordance with the present disclosure.

In an exemplary embodiment shown in FIG. 8, the medical device 800 is a suture including a multifilament elongate body 812, fragments 814 and a needle 822, which may be curved or straight.

In embodiments, bioactive agents may be utilized with the barbed medical device. Bioactive agents may be applied to the elongate body, filaments, and/or construct materials by methods within the purview of those skilled in the art. Such methods include but are not limited to dipping, spraying, brushing, vapor deposition, coextrusion, capillary wicking, film casting, molding, and the like, and combinations of these. In embodiments, the bioactive agent may be localized in the angle formed between the barb and the elongate body of the medical.

Examples of classes of bioactive agents, which may be utilized in accordance with the present disclosure include, for example, anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesion agents that may be utilized in accordance with the present disclosure include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent include, for example, triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent.

Other bioactive agents, which may be included as a bioactive agent include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents, which may be included in the hydrogel include, for example, viruses and cells, including stem cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

Additionally, solvents may be used to incorporate various agents into the barbed medical device. Suitable solvents include polar and non-polar solvents including but not limited to: alcohols such as methanol, ethanol, propanol, and the like, and combinations of these; chlorinated hydrocarbons such as methylene chloride, chloroform, 1,2-dichloro-ethane, and the like, and combinations of these; and aliphatic hydrocarbons such as hexane, heptane, ethyl acetate, and the like, and combinations of these.

Filaments used to make barbed medical devices in accordance with this disclosure can also include, for example, biologically acceptable plasticizers, antioxidants and colorants, which can be impregnated into the filament(s) utilized to form the filaments or included in a coating thereon. In embodiments, barbed medical devices of the present disclosure may be dyed in order to increase the visibility of the device in the surgical field. Any dye suitable for incorporation in implantable medical devices can be used. Such dyes include, but are not limited to, carbon black, bone black, D&C Green No. 6, and D&C Violet No. 2.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments of the present disclosure. Various modifications and variations of the components used to form the surgical implant, as well as methods of delivering the components will be apparent to those skilled in the art from the foregoing detailed description. For example, in embodiments, the barbed medical device may incorporate a loop or knot at one end thereof configured to enhance retention of the device in body tissue at a desired position. Such modifications and variations are intended to come within the scope and spirit of the claims appended hereto.

I claim:

1. A barbed medical device comprising:
   a suture comprising a multifilament tubular braided structure having an outer surface;
   a monofilament fragment having a first portion positioned within the multifilament tubular braided structure and a second portion extending beyond the outer surface of the multifilament tubular braided structure; and
   a surgical needle attached to one or both ends of the tubular braided structure of the suture, wherein the monofilament fragment extends completely through the multifilament tubular braided structure and further comprises a third portion that extends beyond the outer surface of the multifilament tubular braided structure at a location remote from the second portion of the monofilament fragment, and wherein the second and third portions of the monofilament fragment are each configured to anchor into tissue.

2. The barbed medical device in accordance with claim 1, wherein the second portion of the monofilament fragment extends beyond the outer surface of the multifilament tubular braided structure at intervals from about 0.1 mm to about 5 mm.

3. The barbed medical device in accordance with claim 1, wherein the multifilament tubular braided structure further comprises a biocompatible adhesive.

4. The barbed medical device in accordance with claim 1, wherein the monofilament fragment further comprises at least one end portion that forms an angle from about 5° to about 90° with the outer surface of the multifilament tubular braided structure.

5. The barbed medical device in accordance with claim 1, further comprising a bioactive agent.

6. The barbed medical device in accordance with claim 1, wherein the multifilament tubular braided structure further comprises a core.

7. The barbed medical device in accordance with claim 1, wherein the multifilament tubular braided structure comprises yarns.

8. A method of forming a barbed medical device comprising:
   forming a suture comprising a tubular braided structure from a plurality of filaments to form a multifilament tubular braided structure having an outer surface;
   positioning a first portion of a monofilament fragment within the tubular braided structure such that at least a second portion of the monofilament fragment extends beyond the outer surface of the multifilament tubular braided structure to form a barb on the medical device; and
   attaching a surgical needle to one or both ends of the tubular braided structure of the suture, wherein positioning of the monofilament fragment results in the monofilament fragment extending completely through the multifilament tubular braided structure and a third portion of the monofilament fragment extending beyond the outer surface of the multifilament tubular braided structure at a location remote from the second portion of the monofilament fragment, and wherein the second and third portions of the monofilament fragment are each configured to anchor into tissue.

9. The method of claim 8, further comprising re-orienting the second portion of the monofilament fragment.

10. The method of claim 8, wherein forming the tubular braided structure comprises braiding, comingling, weaving, knitting, twisting, aligning, or crinkling a plurality of filaments or yarns.

11. The method of claim 8, further comprising applying a biocompatible adhesive to the filaments.

* * * * *